(12) United States Patent
Hokanson et al.

(10) Patent No.: US 7,282,040 B2
(45) Date of Patent: Oct. 16, 2007

(54) GRAVITATIONAL PRESSURE REGULATING MECHANISM

(75) Inventors: Charles P. Hokanson, Collegeville, PA (US); Bradley S. Smith, Collegeville, PA (US)

(73) Assignee: Vygon US, LLC, Norristown, PA (US)

( * ) Notice: Subject to any disclaimer, the term of this patent is extended or adjusted under 35 U.S.C. 154(b) by 345 days.

(21) Appl. No.: 10/328,895

(22) Filed: Dec. 24, 2002

(65) Prior Publication Data

US 2004/0122348 A1 Jun. 24, 2004

(51) Int. Cl.
*A61M 5/00* (2006.01)

(52) U.S. Cl. .................. 604/9; 604/8; 604/10

(58) Field of Classification Search .............. 604/8–10, 604/19, 93.01, 118, 128, 129, 131, 537, 167.01–167.03, 604/164.01, 164.02, 245–247, 256, 264, 604/523, 175, 288.03; 141/930, DIG. 2; 128/898; 137/215, 216, 216.1–216.2, 217, 137/218, 247, 247.11, 247.13, 247.21, 247.23, 137/251.1, 386, 409–413, 426–430, 449–451, 137/798–799, 906, 910, 247.17, 219
See application file for complete search history.

(56) References Cited

U.S. PATENT DOCUMENTS

| | | | |
|---|---|---|---|
| 2,969,066 A | 1/1961 | Holter et al. | |
| 3,111,125 A | 11/1963 | Schulte | |
| 3,206,160 A * | 9/1965 | Bennett | 251/65 |
| 3,288,142 A | 11/1966 | Hakim | |
| 3,527,226 A * | 9/1970 | Hakim | 604/9 |
| 3,566,876 A | 3/1971 | Stoehr | |
| 3,769,982 A | 11/1973 | Schulte | |
| 3,883,113 A * | 5/1975 | Kolb | 251/209 |
| 3,886,948 A | 6/1975 | Hakim | |
| 3,889,687 A | 6/1975 | Harris et al. | |
| 3,985,140 A | 10/1976 | Harris | |
| 3,991,768 A | 11/1976 | Portnoy | |
| 3,999,553 A | 12/1976 | Spitz et al. | |
| 4,103,689 A | 8/1978 | Leighton | |
| 4,310,017 A | 1/1982 | Raines | |
| 4,332,255 A | 6/1982 | Hakim et al. | |
| 4,354,492 A | 10/1982 | McPhee | |

(Continued)

OTHER PUBLICATIONS

International Search Report dated Apr. 20, 2004, for International Application No. PCT/US03/34359.

*Primary Examiner*—Tatyana Zalukaeva
*Assistant Examiner*—Melanie J Hand
(74) *Attorney, Agent, or Firm*—Caesar, Rivise, Bernstein, Cohen & Pokotilow, Ltd.

(57) ABSTRACT

A gravitational pressure regulating mechanism for use with a valve is provided for control of pressure and diversion of bodily fluids. The mechanism includes a reservoir having first and second ends, the first end being open and the second end having a floor and an entry port, and a free floating weight adapted to freely slide in the reservoir from a closed position wherein the weight is adjacent the floor to an opened position wherein the weight is positioned away from the floor. The weight has a closure member having a surface to engage the entry port when the weight is in the closed position. The mechanism further includes a cap having an exit port to seal the open first end of the reservoir. The mass of the weight is proportional to the amount of resistance to flow of the bodily fluids through the regulating mechanism.

4 Claims, 4 Drawing Sheets

U.S. PATENT DOCUMENTS

| | | |
|---|---|---|
| 4,387,715 A | 6/1983 | Hakim et al. |
| 4,443,214 A | 4/1984 | Marion |
| 4,468,224 A | 8/1984 | Enzmann et al. |
| 4,551,128 A | 11/1985 | Hakim et al. |
| 4,595,390 A | 6/1986 | Hakim et al. |
| 4,610,658 A | 9/1986 | Buchwald et al. |
| 4,615,691 A | 10/1986 | Hakim et al. |
| 4,621,654 A * | 11/1986 | Holter ................. 137/38 |
| 4,673,384 A | 6/1987 | Marion |
| 4,676,772 A | 6/1987 | Hooven |
| 4,681,559 A | 7/1987 | Hooven |
| 4,729,762 A | 3/1988 | Doumenis |
| 4,787,886 A | 11/1988 | Cosman |
| 4,787,887 A | 11/1988 | Arroyo |
| 4,795,437 A | 1/1989 | Schulte et al. |
| 4,867,741 A | 9/1989 | Portnoy |
| 5,042,974 A | 8/1991 | Agarwal |
| 5,192,265 A | 3/1993 | Drake et al. |
| 5,336,166 A | 8/1994 | Sierra |
| 5,634,894 A | 6/1997 | Magram |
| 5,643,195 A | 7/1997 | Drevet et al. |
| 5,690,117 A | 11/1997 | Gilbert |
| 6,090,062 A | 7/2000 | Sood et al. |
| 6,126,628 A | 10/2000 | Nissels |
| 6,383,160 B1 | 5/2002 | Madsen |
| 7,118,549 B2 * | 10/2006 | Chan ................. 604/10 |
| 2002/0026139 A1 | 2/2002 | Bertrand et al. |
| 2002/0128588 A1 | 9/2002 | Borgesen |

* cited by examiner

GRAVITATIONAL PRESSURE REGULATING MECHANISM

BACKGROUND OF THE INVENTION

This invention relates to a shunt valve for draining of cerebrospinal fluid.

In the treatment of hydrocephalus, it has been customary to drain excess cerebrospinal fluid (CSF) from one site in the body to another. For example, a catheter may be introduced into the ventricle within the brain and connected through a pressure operated check valve to a subcutaneous catheter so that the CSF is introduced into the blood stream or the peritoneal cavity. Alternatively, a catheter may be inserted into the body adjacent the spine and connected through a check valve to a catheter inserted in the peritoneal cavity. The latter is commonly termed a lumbar peritoneal shunt system and may be employed only upon patients afflicted with communicating hydrocephalus in which the excess CSF is not confined to the cranium, but is present in the region of the spine.

The invention of the first functioning hydrocephalus shunt was made in 1956 as disclosed in U.S. Pat. No. 2,969,066 (Holter). Numerous improvements and changes were made to this invention as described in further detail below. However, problems such as overdrainage of CSF continues to be a major cause of shunt malfunction and revision.

Shunt systems of this general sort are disclosed in U.S. Pat. Nos. 3,288,142 (Hakim) and 3,527,226 (Hakim). These shunt systems do not satisfactorily solve a problem brought about by the pressure drop which results when the patient shifts from a substantially horizontal to a substantially vertical position. The check valves normally include a spring action to keep the valves closed until the CSF pressure rises to a predetermined pressure setting of the valve. However, in the case of a patient fitted with a lumbar peritoneal shunt system, the hydrostatic head, working upon the check valve, increases abruptly when he moves from a horizontal to vertical position, and the pressure increase causes the valve to open. The result is excessive rate of drainage. The similar rate of drainage change is caused by the length of the drainage tubing on a ventriculo atrial or ventriculo peritoneal shunt system as the patient moves from horizontal to vertical.

In 1976, in an attempt to minimize the risk of overdrainage, U.S. Pat. No. 3,991,768 (Portnoy) issued that was directed to an anti-siphon device to control the flow of CSF which occurs when a patient rises from a supine position. Here, the shunt system drains fluid from one region of the human body and discharges it into another in which means is included to resist overdrainage or siphoning of the region as a consequence of low downstream hydrostatic pressures. The system includes a collector catheter and a discharge catheter, and a valve that interconnects these catheters to open the system to flow, or to close it to flow, as a consequence of the position of its closure means which is responsive to the pressure differential between the pressure in the valve as transmitted by the catheters, and a reference pressure such as the atmosphere. The concept behind this device was that maintaining the pressure at a constant, positive value minimizes the risk of overdrainage and the complications that result. The anti-siphon device maintained the differential pressure across the valve close to atmospheric pressure, suppressing the hydrostatic column that forms in the distal catheter when the patient stands.

U.S. Pat. No. 4,795,437 (Schulte et al.) modifies the invention of Portnoy and discloses a subcutaneously implantable siphon control device for use in a shunt system. The device includes a proximal catheter, a flow control valve and a distal catheter. The siphon control device limits fluid flow through the shunt system due to the siphoning effect of negative hydrostatic pressure created by the elevation of the proximal catheter inlet with respect to the distal catheter outlet. The siphon control device includes a base having an inlet placed in fluid communication with an outlet of the flow control valve, and an outlet placed in fluid communication with the distal catheter, and a housing for the base which, in connection with the base, defines a fluid flow pathway between the inlet and the outlet. The base provides a wall having substantially parallel upper and lower seating surfaces, which separates the inlet from the outlet. A pair of spaced, substantially parallel, flexible and elastic diaphragms having inner and outer surfaces are provided by the housing, and are situated on opposite sides of the wall to position a portion of each inner surface in contact with an adjacent one of the seating surfaces. Unfortunately, a high rate of complications due to both under and over drainage still occurred with the use of an anti-siphon device. In addition, the anti-siphon device introduced the entirely new complication of occlusion due to tissue encapsulation.

Subsequently, in 2000, U.S. Pat. No. 6,090,062 (Sood et al.) issued which discloses a programmable anti-siphon device which, while still susceptible to tissue encapsulation, incorporates a feature which permits the relationship between the seat and membrane to be adjusted to compensate for tissue encapsulation or increased or decreased levels of anti-siphon pressure.

In 2002, U.S. Pat. No. 6,383,160 (Madsen) disclosed a variable anti-siphon device for use in cerebrospinal fluid shunt systems. The devices include a housing with an internal chamber, an adjustable barrier separating the chamber into two cavities, and a diaphragm that seats itself against the adjustable barrier with a seating force that is proportional to the pressure differential across it. The adjustable barrier allows the level of anti-siphon protection to be modified. In one embodiment, the height of the adjustable barrier may be varied. In another embodiment, the barrier is moved longitudinally within the internal chamber to vary the volume of each chamber. This device modifies the invention of U.S. Pat. No. 6,090,062 (Sood et al.) by permitting non-invasive adjustment.

The above designs suffer from several problems. First, they depend upon an elastomeric membrane, which, by virtue of the properties of elastomers, tend to increase in stiffness over time, thereby changing the functional properties of the membrane. Additionally, these pressure sensitive membranes are in contact with surrounding tissue and may be pressed upon by scar tissue, encapsulating the mechanism, thereby increasing the pressure necessary to overcome the encapsulation. Furthermore, these devices are generally implanted on the cranium under the scalp, and may be occluded by the weight of the skull resting on the device when the patient is recumbent. Finally, in order for these devices to be sufficiently sensitive to changes in pressure, the membranes must be very thin and delicate. They may be easily damaged or destroyed by puncture with a needle, which may occur whenever CSF samples are taken or medication is administered through the shunt.

U.S. Pat. No. 3,889,687 (Harris et al.) discloses a shunt system for the transport of cerebrospinal fluid that compensates for overdrainage by the use of a gravity and attitude activated device consisting of a pressure valve mechanism and separate multiple ball-in-cylinder design. When properly implanted with the axial dimension of the valve cylinder parallel to the vertical axis of the patient, the balls are free to move within the cylinder and the intracranial pressure (ICP) is controlled by the pressure valve. Here, when the patient rises from the recumbent to the standing or sitting position, placing the ball and cylinder in the vertical position, the balls bias against the inlet of the cylinder and the weight of the balls increase the system pressure to prevent over drainage. Unfortunately, this device is bulky and highly position sensitive, and only works properly in the vertical position. This design was designed to be implanted on the patient's side, above the waist, at the level of entry of the lumbar catheter into the spine, to be used with a lumbar catheter for drainage of CSF from the lumbar space. An additional problem was that the cylinder and balls, as well as the differential valve mechanism, were made of stainless steel, which causes an artifact on CT or MRI imaging. This is especially troublesome, as lumbar catheter placement leads to a higher complication rate of spine problems, thereby necessitating imaging of the exact area which is compromised by the magnetic implant.

U.S. Pat. No. 5,042,974 (Agarwal) discloses a shunt valve for draining cerebrospinal fluid. The shunt valve includes a deformable housing having a proximal and distal end. A non-deformable valve chamber is disposed within the housing to form an inlet chamber with the distal end and an outlet chamber with the proximal end. The shunt valve has an inlet into the inlet chamber and an outlet from the outlet chamber. The flow of the fluid within the shunt valve is a Z-flow path and the inlet and outlet are provided along the same axis. This design modifies the design of the Harris '687 patent discussed above. Here, the valve mechanism is eliminated thereby reducing the size and bulk such that the device is suitable for placement under the scalp next to the posterior portion of the cranium, such that it is parallel to the vertical axis of the patient when the patient is standing or sitting. However, to function properly as a shunt, the device must be used in conjunction with an anti-reflux mechanism. Additionally, this device was manufactured from stainless steel thereby compromising CT and MRI images.

U.S. Pat. No. 3,769,982 (Schulte et al.) is directed to a physiological drainage system with closure means responsive to downstream suction. The system is for draining liquids from a source of the human body to a region where it is disposed of. The latter region is at a different elevation from the source region. The system is provided with a control which is responsive to downstream suction. When the suction is excessive, the control closes the system to flow so as to prevent over-drainage of the source region. The control comprises a valve which remains open to flow at normal rates and downstream suction levels, and which closes when the downstream suction level is above a predetermined level.

U.S. Pat. No. 4,621,654 (Holter) is directed to an attitude and pressure responsive valve assembly. This valve assembly is for relieving intracraneal pressure and includes a valve housing adapted for implantation and having an inlet port for connection to a ventricular catheter and an outlet port for connection to a venous or peritoneal catheter. The valve housing includes a fluid passage, the flow through which is controlled by a first pressure sensitive valve of relatively high resistance and a second pressure responsive valve of relatively low resistance. An attitude responsive valve is disposed in the fluid passage in parallel with the first pressure responsive valve. The valve assembly is implanted in a patient with the attitude responsive valve in a closed position when the patient is in an upright position and in an open position when the patient is in a horizontal position. The employment of pressure responsive and attitude responsive valves in parallel provides ventricular pressure relief regardless of the patient's position.

U.S. Pat. No. 4,443,214 (Marion) discloses a valve adapted to be inserted between a ventricular catheter and a draining catheter and comprises a body of a flattened cylindrical shape enclosing a chamber having formed through its cylindrical wall an inlet passage for introducing the cephalorachidian fluid and an outlet passage for discharging this fluid. At the inner end of the inlet passage, a frustoconical seat engageable by a ball valve acting as a non-return valve is provided. This ball valve is urged against the seat by a curved spring blade extending along the lateral inner wall of the chamber and is mounted in overhanging relationship on a diameter bar of magnetic material mounted in turn for concentric rotation on a pivot pin extending across the chamber. A tooth carried by the bar end opposite the spring blade engages detent-positioning dents formed in the lateral wall of the chamber.

U.S. Pat. No. 4,595,390 (Hakim et al.) discloses a surgically-implantable shunt valve for venting CSF in the treatment of hydrocephalus in which popping (pulsing) pressure is adjusted in finite increments by application of an external magnetic field.

U.S. Pat. No. 4,615,691 (Hakim et al.) discloses a surgically implantable stepping motor isolated physically from electrical power sources and powered by a magnetic field applied from outside the apparatus.

U.S. Pat. No. 6,126,628 (Nissels) discloses a device for limiting the flow of a fluid from a first region of a patient's body to a second region. The device includes a primary passage for directing fluid from an inlet of the device to an outlet in response to the fluid flow rate being less than a predetermined level and a secondary passage for directing fluid from the inlet to the outlet in response to the flow rate being greater than or equal to the predetermined level. The secondary passage is a tortuous flow path and presents a higher resistance to fluid flow than the primary passage. A detector closes the primary passage in response to the flow rate reaching the predetermined level in order to force the fluid to pass through the secondary passage. When the fluid flow rate reaches overdrainage, the fluid is forced through the secondary passage in order to effectively reduce the fluid flow rate and prevent overdrainage. As soon as the flow rate decreases below the predetermined level, the primary passage opens itself automatically.

U.S. Pat. No. 3,111,125 (Schulte) discloses a drainage device that includes a diaphragm-type pump and a conduit to form shunt connections with various parts of the human body to relieve one of the parts of undesirable accumulations of fluids.

U.S. Pat. No. 4,787,887 (Saenz Arroyo) discloses a ventricular by-pass device for draining the cephalorachidian liquid in the hydrocephalus. It consists of a check valve device which obstructs the brain suction orifice. Its valve controls the flow of fluid in the shunt system according to the differences in pressure at a point inside the valve and the pressure in a bodily region outside and near the valve.

U.S. Pat. No. 5,643,195 (Drevet et al.) discloses a device for regulating the flow of an organic liquid between a production site and a resorption site of a patient in a drainage circuit that extends between the two sites where one of the sites is a site of small pressure variation and the other is a site of large pressure variation. Pressure is regulated particularly as a function of the position of the patient.

All references cited herein are fully incorporated herein by reference in their entireties.

BRIEF SUMMARY OF THE INVENTION

The present invention provides a device that is simple to make and use, is reliable and precise, and is nonmagnetic so as not to compromise CT and MRI images. In addition, the present invention permits independent use or use in combination with standard valve systems to compensate for their functional deficiencies while permitting a physician to use a valve mechanism that he or she is familiar with. Finally, the device provides an increased level of safety for the patient.

The invention relates to an implantable gravitational pressure regulating mechanism which, when attached to a valve, becomes a gravitational pressure regulating valve for the control of pressure and diversion of bodily fluids such as CSF.

The present invention is directed to a gravitational pressure regulating mechanism for use with a valve for control of pressure and diversion of bodily fluids. In a first preferred embodiment, a gravitational pressure regulating mechanism for control of pressure and diversion of bodily fluids is provided which includes a reservoir having an entry port and an exit port, a free floating weight adapted to freely slide in the reservoir from a closed position wherein the weight blocks the entry port to an opened position wherein the weight is positioned away from the entry port and a cap to seal the exit port. The mass of the free floating weight is proportional to the amount of resistance to flow of the bodily fluids through the regulating mechanism. Preferably, the free-floating weight is generally cylindrical in shape. Finally, the weight may have an aperture extending through it to permit a minimal flow of bodily fluids entering from the exit port to the exit port while the weight is in the closed position.

In another preferred embodiment, the mechanism includes a reservoir having first and second ends, the first end being open and the second end having a floor and an entry port, and a free floating weight adapted to freely slide in the reservoir from a closed position wherein the weight is adjacent the floor to an opened position wherein the weight is positioned away from the floor. The weight has a closure member having a surface to engage the entry port when the weight is in the closed position. The mechanism further includes a cap having an exit port to seal the open first end of the reservoir. The mass of the weight is proportional to the amount of resistance to flow of the bodily fluids through the regulating mechanism. Again, preferably, the free-floating weight is generally cylindrical in shape.

The floor of the reservoir is preferably generally conically-shaped with the entry port at the center of conically-shaped floor. Preferably, the reservoir and free-floating weight are manufactured from biocompatible non-ferrous materials, preferably of greater than or equal specific gravity than stainless steel such as Elgiloy®, Phynox™, or tantalum. The surface adapted to engage the entry port when the weight is in the closed position may be constructed in an integral unit with the weight or separately attached to the weight. The surface may be a protrusion having a shape that is, for example, conical, flat, hemispherical, curved, tapered, or needle. The closure member of the weight may help to center the weight in the reservoir.

The weight may have a series of channels to permit unrestricted flow of a portion of the bodily fluids entering the mechanism from the entry port to the exit port. Preferably, the cap is constructed from an elastomeric material. Additionally, preferably, the closure member is constructed from sapphire, ruby, or synthetic ceramic, and, more preferably, from one of these materials in the shape of a hemisphere. It is desirable that the distance between an end of the weight opposite the closure member and an inside surface of the elastomeric cap is less than a height of the weight. Finally, the weight may have an aperture extending through it to permit a minimal flow of bodily fluids entering from the exit port to the exit port while the weight is in the closed position.

In an alternate embodiment, the entry port extends above the floor as a tube into the reservoir and the weight is adapted to pivot on the tube. Here, as the mechanism is moved from a vertical position to a horizontal position (e.g., the patient lays down), the weight pivots about the tube such that an opening in the tube created by the entry port and the closure surface increases in dimension until fully opened. In this embodiment, a gravitational pressure regulating mechanism for control of pressure and diversion of bodily fluids is provided which includes a reservoir having an entry port and an exit port where the entry port extends above the floor as a tube into the reservoir. The mechanism further includes a weight having a closure surface on an end thereof where the weight is adapted to rotate in the reservoir from a closed position where the closure surface blocks the entry port to an opened position wherein the entry port is open. The mechanism includes a cap to seal the exit port. The weight pivots on the tube whereby as the mechanism is moved from a vertical position to a horizontal position, an opening in the tube created by the entry port and the closure member increases in dimension until fully opened. Finally, the weight may have an aperture extending through it to permit a minimal flow of bodily fluids entering from the exit port to the exit port while the weight is in the closed position.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
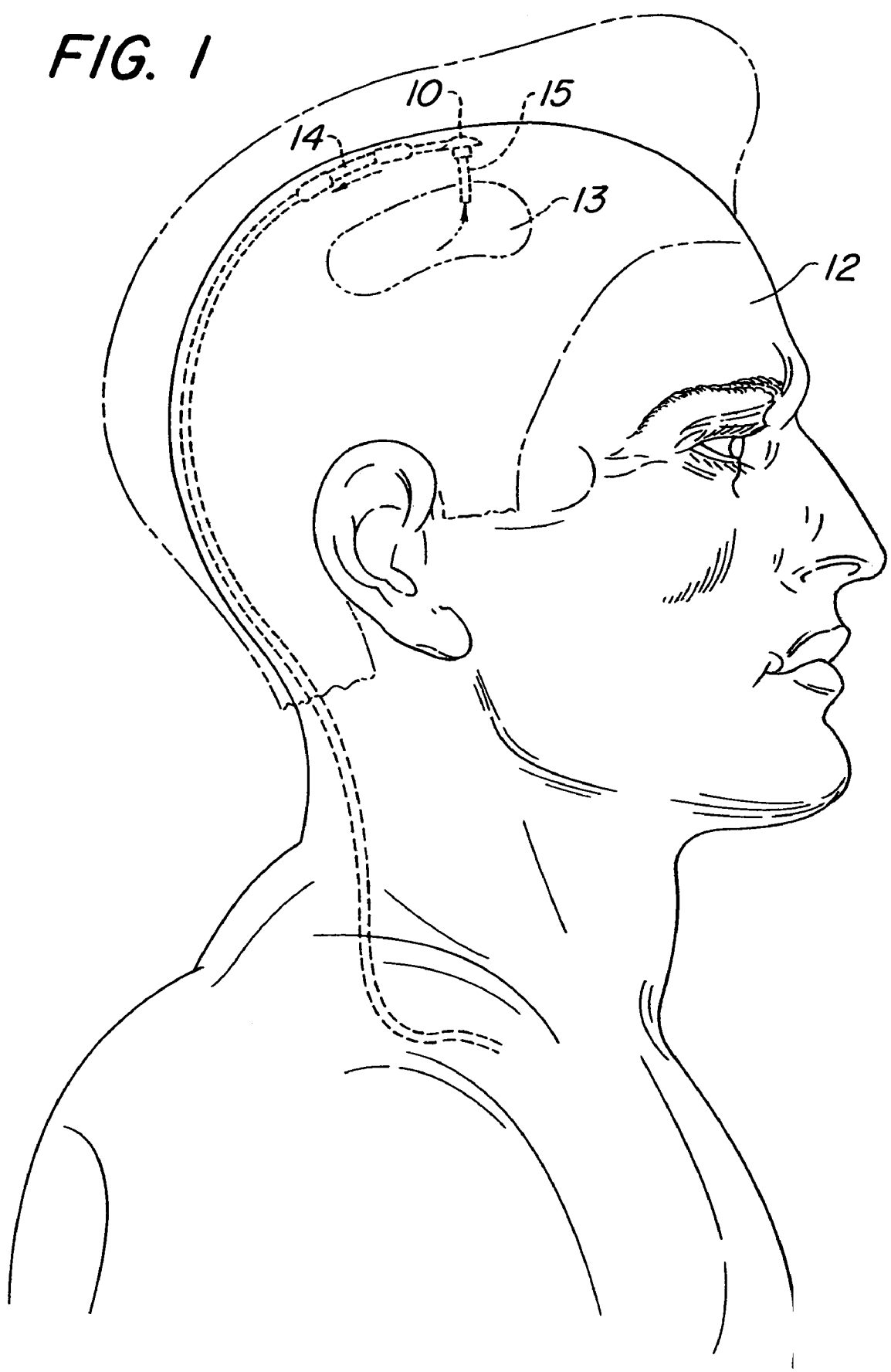
FIG. 1 is a side, elevational view of a gravitational pressure regulating mechanism with a valve assembly as attached to a human being.

Referring now to the drawing figures, wherein like part numbers refer to like elements throughout the several views, there is shown in FIG. 1, a gravitational pressure regulating mechanism 10 as attached to a human being 12 which also includes a valve assembly 14. The gravitational pressure regulating mechanism 10 is mounted to the crown of the skull in a hole drilled into the crown and is a attached to a catheter 15 that is introduced into the ventricle 13 within the brain. Placement of the reservoir on the crown of the head is necessary. Frontal horn catheter placement is preferable. As seen in FIG. 1, fluid is drained through the regulating mechanism 10, through valve assembly 14 and into a remote part of the body, as known to those skilled in the art for similar devices.

As can be seen in FIGS. 2-5, the gravitational pressure regulating mechanism 10 consists of a free-floating weight 16, contained within a rigid reservoir 18. The reservoir 18 has a first end 18a and a second end 18b. The first end 18a is open and the second end 18b has a floor and a bottom entry port 20. The open first end 18a is covered by an elastomeric cap 22 which has a side arm exit port 24. The reservoir 18 has floor 26, preferably having a conical configuration, with the entry port 20 at the center of the floor 26 forming a seat. The floating weight 16 is preferably generally cylindrical in shape and has a closure member 28 at its base 30, which is designed to bias against the seat formed by the conical floor 26 and entry port 20 of the reservoir 18. "Cylindrical" in accordance with the present invention is intended to broadly cover shapes that are generally cylindrical. That is, shapes that have a top and a generally parallel bottom end with a cross-section that is at least somewhat circular in configuration. This circular cross-section is intended to cover cross sections that have portions of the cross-section removed, for example, for channels and the like.

Figure 2:
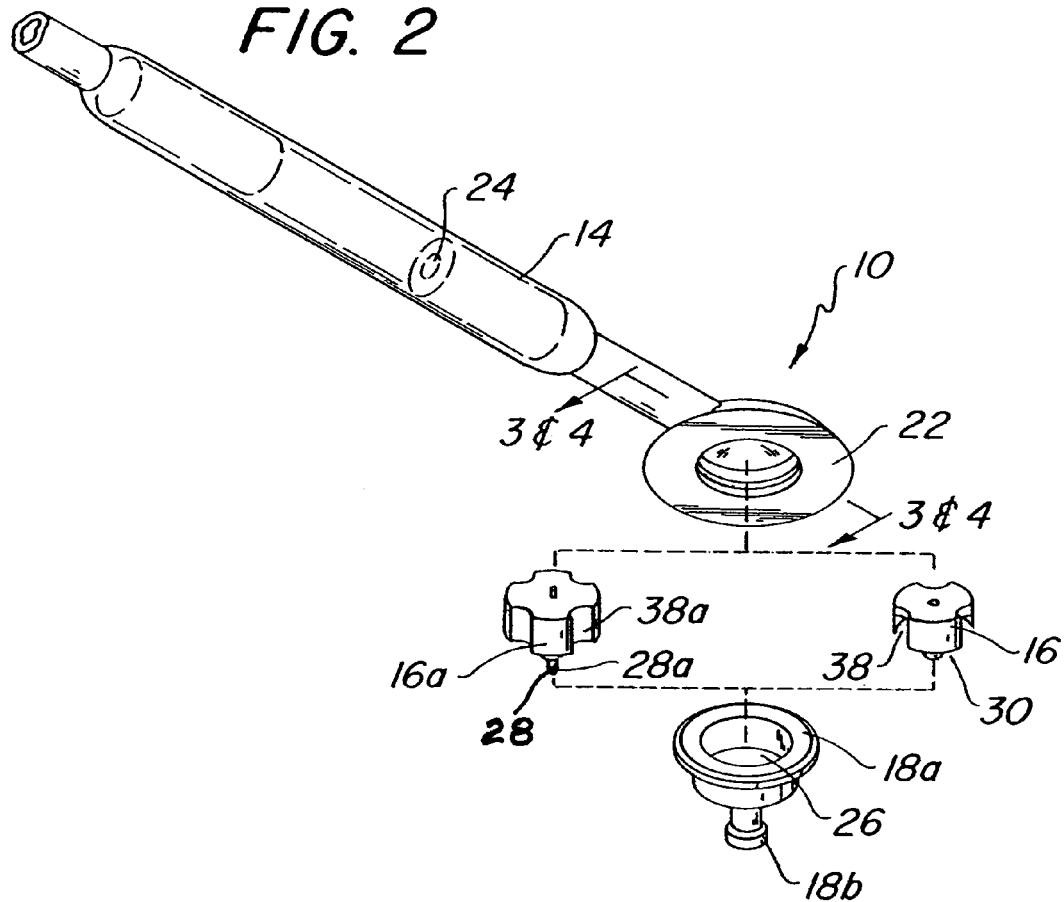
FIG. 2 is an isometric view of the gravitational pressure regulating mechanism of FIG. 1 and depicts two alternate examples of free-floating weights that may utilized.
Figure 3:
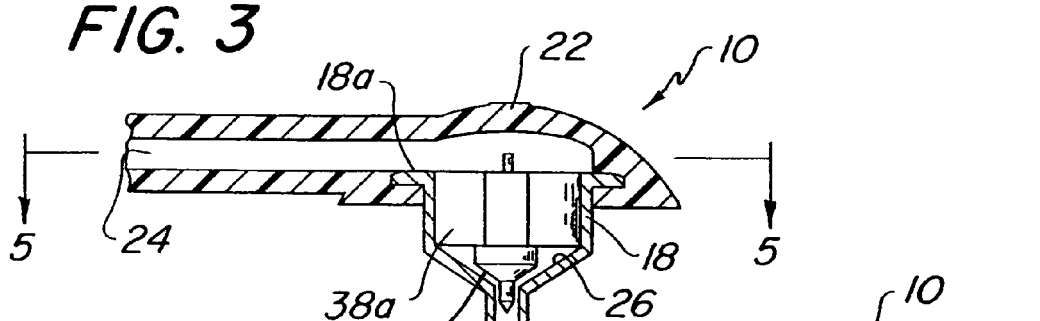
FIG. 3 is a partial, cross-sectional, elevational view of the gravitational pressure regulating mechanism of FIG.1, taken substantially along lines 3--3 of FIG. 2 depicting use of a first example of the two alternate examples of free-floating weights.
Figure 4:
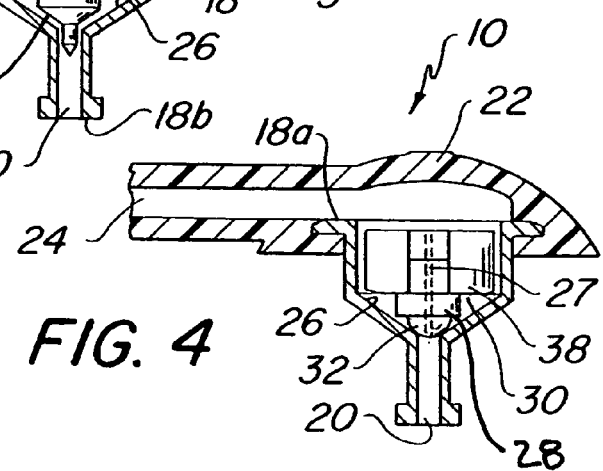
FIG. 4 is a partial, cross-sectional, elevational view of the gravitational pressure regulating mechanism of FIG.1, taken substantially along lines 4--4 of FIG. 2 depicting use of a second example of the two alternate examples of free-floating weights.
Figure 5:
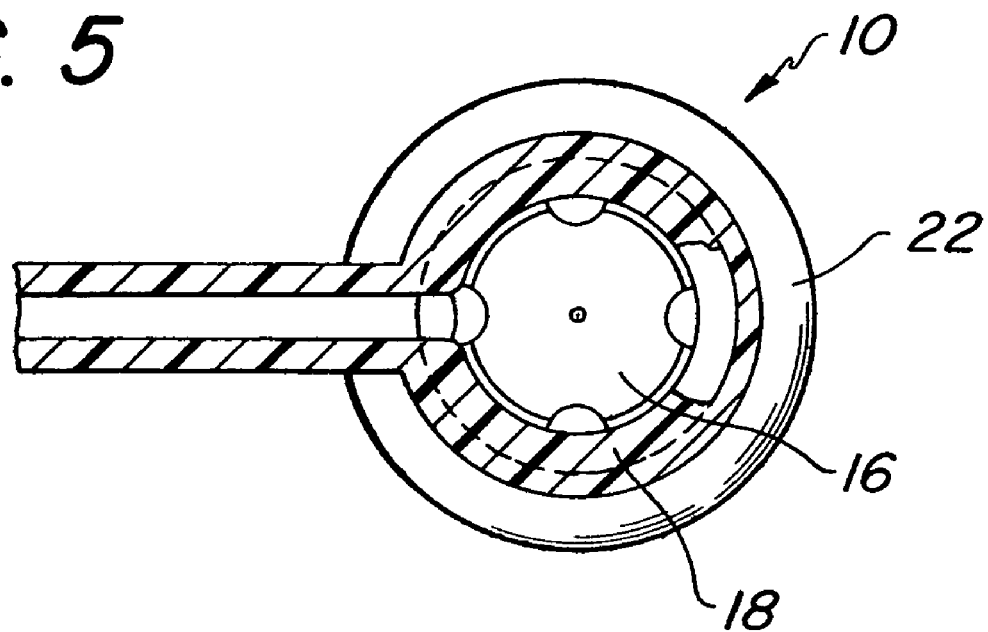
FIG. 5 is a partial, cross-sectional view of the gravitational pressure regulating mechanism of FIG. 1, taken substantially along lines 5--5 of FIG.3.

The free-floating weight 16 must have a surface 32 to act as a closure mechanism. This surface 32 may be a machined or molded integral part of the floating weight 16 or it may be separately attached. The surface 32 may have many different shapes, all of which are designed to provide a seal of the orifice formed by the entry port 20 on the conical floor 26 at the bottom center of the reservoir 18, when the center of gravity of the weight 16 is positioned over or substantially over the bottom entry port 20. For example, the closure member surface 32 may be, for example, a V-shaped, flat, or curved surface. Alternatively, as can be seen in FIGS. 2 and 3, the closure member surface 32 of the weight 16a may be, for example, a tapered needle-shaped (or pin-shaped) protrusion surface 28a designed to fit into the bottom entry port 20 of the reservoir 18. In this configuration, the needle-shaped protrusion surface 28a also acts as a centering guide for the weight 16a, ensuring that the weight 16a is always centered upon the entry port 20 whenever the floating weight 16a is above the entry port 20. Additionally, the needle-shaped protrusion surface 28a may be shaped to create an appropriate level of resistance at various attitudes of the regulating mechanism 10. Optionally, as can be seen in FIG. 4, the weight may have a small aperture 27 that extends vertically through the weight 16. This aperture 27 permits some small flow initially while the weight 16 is seated. A greater force would then be required to dislodge the weight 16 from is sealed position.

In this preferred embodiment of the gravitational pressure regulating mechanism 10, the outside diameter of the free-floating weight 16 is slightly smaller than the inside diameter of the reservoir 18, for example, one or two thousandths of an inch, permitting unrestricted movement of the weight 16 with respect to the reservoir 18 in the vertical axis of the reservoir 18. As can be seen in FIGS. 3 and 4, the height of the free-floating weight 16 is preferably equal to or slightly less than the height of the interior vertical walls of the reservoir 18. The free-floating weight 16 has a multiplicity of channels 38, 38a, the spacing of each being equidistant from one another, running from top to bottom along the outer surface of the weight 16. The channels 38 permit unrestricted flow of fluid from the bottom entry port 20 at the second end 18b of the reservoir 18 through the side arm exit port 24 in the elastomeric cap 22, whenever the closure member 28 on the free floating weight 16, is displaced from the entry port 20. The generally cylindrical configuration of the free-floating weight facilitates use of the channels 38.

The preferred embodiment of the weight 16 is a two-piece unit formed by placing a sapphire ball 32a in a receptacle in the center of the bottom of the free floating weight 16, as best shown in FIGS. 3 and 4. The fit of the weight 16 within the reservoir 18 and the conical floor 26 of the reservoir 18 act to position the ball 32a directly over the bottom entry port 20. The elastomeric cap 22 is designed to fit over the reservoir 18 in a fixed position. The distance between the top of the weight 16 and the inside dome 22a of the elastomeric cap 22 is preferably less than the vertical height of the weight 16. This is to ensure that the free-floating weight 16 is never dislodged from the reservoir 18, even if the entire gravitational pressure regulating mechanism 10 is inverted. A sapphire spherical shape is particularly useful in that sapphire may by manufactured that have a very smooth surface for providing excellent sealing.

Figure 7:
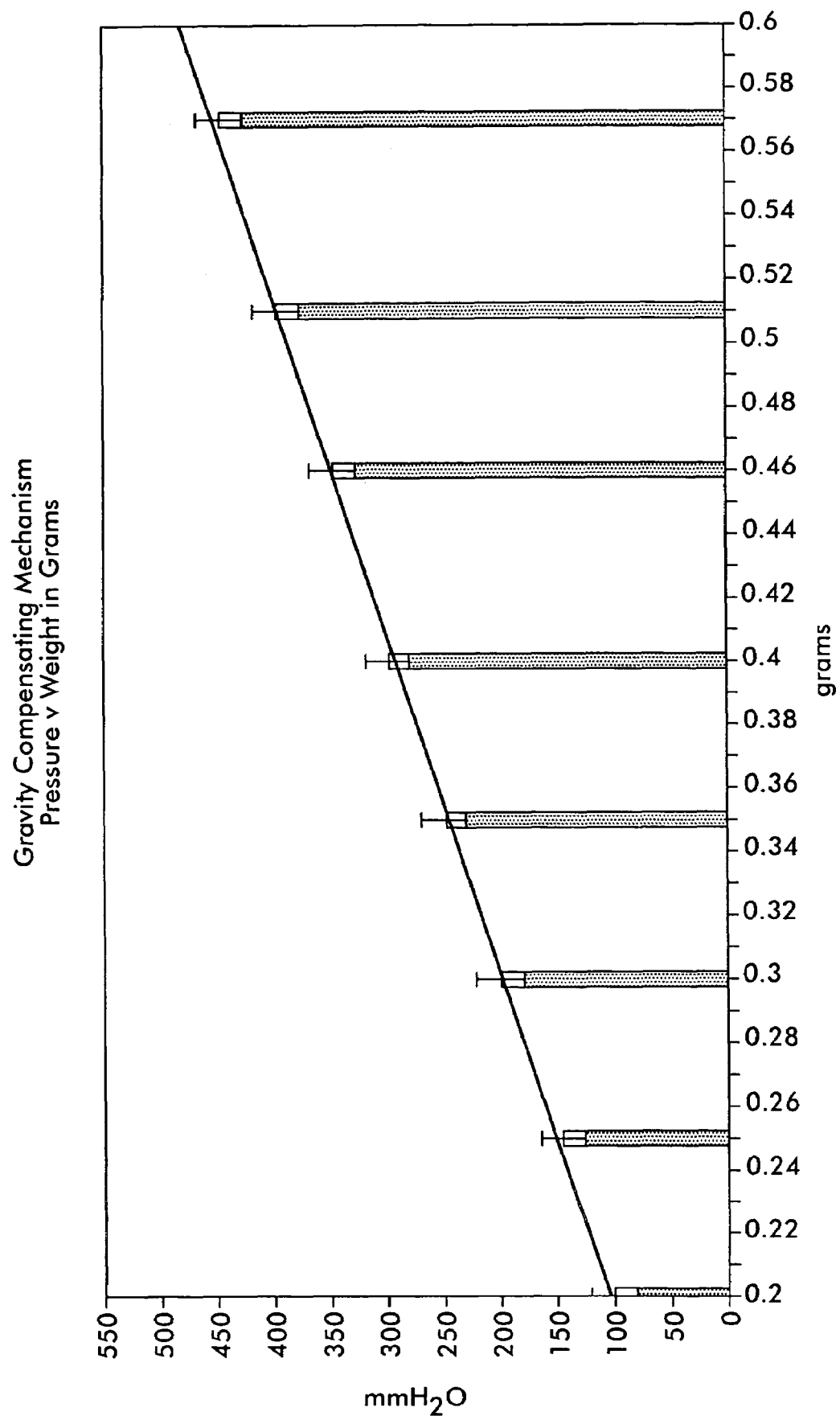
FIG. 7 is a graphical representation of an example of pressure created by the gravitational pressure regulating mechanism of FIG. 1 versus weight of free floating weight utilized in the mechanism.

As seen in the graphical representation of FIG. 7, the amount of resistance to over drainage provided by the gravitational pressure regulating mechanism 10 is directly proportional to the weight (mass) of the free floating weight 16 (or 16a). The free floating weight 16 may be made of any acceptable biocompatible material such as 316 surgical stainless steel. To minimize or avoid imaging artifacts, such as CT and/or MRI artifacts, it is preferable to use a biocompatible non-ferrous material, preferably of equal or greater specific gravity than stainless steel, such as Elgiloy, Phynox, tantalum, or other similar biocompatible substance. The mass of the cylindrical weight 16 may be varied, for example, by boring portions of the weight 16 out or by using selecting one of various materials that has a desired density. As seen in FIG. 2, floating weight 16a uses a substantially greater amount of material than that of floating weight 16. However, by selecting materials having different densities, floating weight 16a may be manufactured to weigh substantially the same amount as that of floating weight 16 where floating weight 16 is manufactured from a material of higher density than that of floating weight 16.

Figure 6:
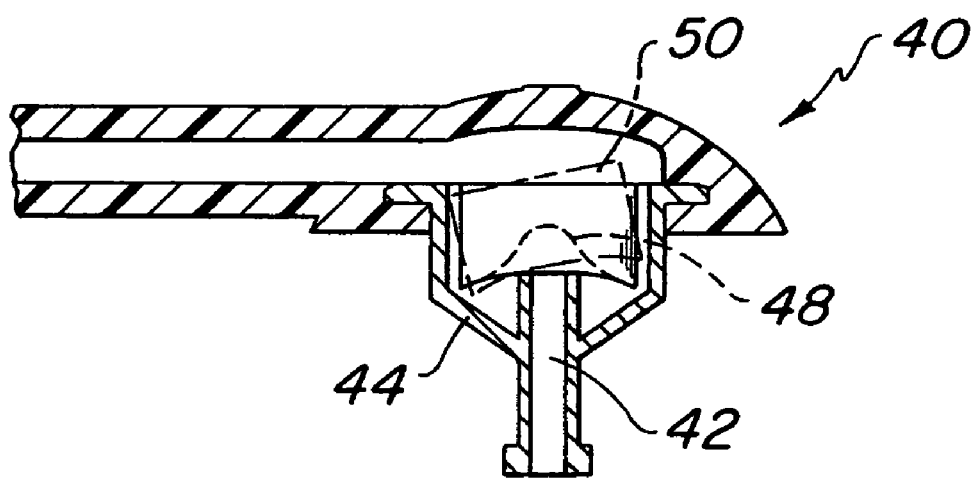
FIG. 6 is a partial, cross-sectional, elevational view of an alternate gravitational pressure regulating mechanism similar to that shown in FIGS. 2-5.

In an alternate embodiment of the gravitational pressure regulating mechanism 40 as shown in FIG. 6, the wall of the bottom entry port 42 extends upwardly (with respect to the perspective of FIG. 6) into the center of the reservoir 44 above the floor 46 of the reservoir 44, and the free-floating weight 50 preferably has a recess 48 or dimple designed to accept the extended entry port 42. Whenever the weight 50 is centered above the entry port 52, the weight 50 biases against the extended entry port 42 to form a seal. As the gravitational pressure regulating mechanism 40 is moved from the vertical to the horizontal axis, the weight 50 pivots on the extended entry port 42 and the opening between the entry port 42 and weight 50 increases in dimension until fully open when the weight 50 is resting towards its side.

As can be seen in FIG. 1, the gravitational pressure regulating mechanism 10 (or alternate embodiment of the mechanism 40) is connected to the valve assembly 14. The valve assembly may be any type of valve assembly, known to those skilled in the art, that will operate properly to provide an anti-siphon action.

While the invention has been described in detail and with reference to specific examples thereof, it will be apparent to one skilled in the art that various changes and modifications can be made therein without departing from the spirit and scope thereof.

What is claimed is:

1. A gravitational pressure regulating mechanism for control of pressure and diversion of bodily fluids, for placement on a living being, comprising:
    (a) a reservoir having an entry port and an exit port, said reservoir for placement on a crown of a head of the living being;
    (b) a free floating weight having a closure member on an end thereof, the weight freely slidable in the reservoir from a closed position wherein the closure member blocks the entry port to an opened position, wherein the weight is positioned away from the entry port, wherein the weight has a plurality of channels to permit unrestricted flow of a portion of the bodily fluids entering the mechanism from the entry port to the exit port; and
    (c) a cap to seal the exit port;
    whereby the mass of the free floating weight is proportional to the amount of resistance to flow of the bodily fluids through the regulating mechanism.

2. A gravitational pressure regulating mechanism for control of pressure and diversion of bodily fluids, for placement on a living being, comprising:
    (a) a reservoir having an entry port and an exit port, said reservoir for placement on a crown of a head of the living being;
    (b) a free floating weight having a closure member on an end thereof the weight freely slidable in the reservoir from a closed position wherein the closure member blocks the entry port to an opened position wherein the weight is positioned away from the entry port, wherein the weight has an aperture extending therethrough to permit a minimal flow of bodily fluids entering from the exit port to the exit port while the weight is in the closed position; and
    (c) a cap to seal the exit port;
    whereby the mass of the free floating weight is proportional to the amount of resistance to flow of the bodily fluids through the regulating mechanism.

3. A gravitational pressure regulating mechanism for use with a valve for control of pressure and diversion of bodily fluids, for placement on a living being, comprising:
    (a) a reservoir having a first end and a second end, the first end being open and the second end having a floor and an entry port, said reservoir for placement on a crown of the head of the living being;
    (b) a free floating weight freely slidable in the reservoir from a closed position wherein the weight is adjacent the floor of the reservoir to an opened position wherein the weight is positioned away from the floor of the reservoir, the weight having a closure member on an end of the weight, the closure member having a surface to engage the entry port when the weight is in the closed position, wherein the weight has a plurality of channels to permit unrestricted flow of a portion of the bodily fluids entering the mechanism from the entry port to the exit port; and
    (c) a cap to seal the open first end of the reservoir, the cap having an exit port;
    whereby the mass of the free floating weight is proportional to the amount of resistance to flow of the bodily fluids through the regulating mechanism.

4. A gravitational pressure regulating mechanism for use with a valve for control of pressure and diversion of bodily fluids, for placement on a living being, comprising:
    (a) a reservoir having a first end and a second end, the first end being open and the second end having a floor and an entry port, said reservoir for placement on a crown of the head of the living being;
    (b) a free floating weight freely slidable in the reservoir from a closed position wherein the weight is adjacent the floor of the reservoir to an opened position wherein the weight is positioned away from the floor of the reservoir, the weight having a closure member on an end of the weight, the closure member having a surface to engage the entry port when the weight is in the closed position, wherein the weight has an aperture extending therethrough to permit a minimal flow of bodily fluids entering from the exit port to the exit port while the weight is in the closed position, and
    (c) a cap to seal the open first end of the reservoir, the cap having an exit port;
    whereby the mass of the free floating weight is proportional to the amount of resistance to flow of the bodily fluids through the regulating mechanism.

* * * * *